(12) United States Patent
Giessler-Blank et al.

(10) Patent No.: US 9,126,163 B2
(45) Date of Patent: Sep. 8, 2015

(54) NANOEMULSIONS AND PROCESSES FOR THEIR PREPARATION, AND THEIR USE AS FORMULATIONS OF PLANT PROTECTION AGENTS AND/OR PESTICIDES AND/OR COSMETIC PREPARATIONS

(75) Inventors: Sabine Giessler-Blank, Dortmund (DE); Ralph Scheuermann, Essen (DE); Joachim Venzmer, Essen (DE); David Lindsay, Chester, VA (US)

(73) Assignee: Evonik Degussa GmbH, Essen (DE)

(*) Notice: Subject to any disclaimer, the term of this patent is extended or adjusted under 35 U.S.C. 154(b) by 142 days.

(21) Appl. No.: 12/540,716

(22) Filed: Aug. 13, 2009

(65) Prior Publication Data
US 2010/0041629 A1 Feb. 18, 2010

Related U.S. Application Data

(60) Provisional application No. 61/089,079, filed on Aug. 15, 2008.

(51) Int. Cl.
| | | |
|---|---|---|
| A61K 9/00 | (2006.01) | |
| B01F 17/54 | (2006.01) | |
| A01N 25/04 | (2006.01) | |
| A61K 8/06 | (2006.01) | |
| A61K 8/894 | (2006.01) | |
| A61Q 19/00 | (2006.01) | |
| B01F 17/00 | (2006.01) | |

(52) U.S. Cl.
CPC ............ *B01F 17/0071* (2013.01); *A01N 25/04* (2013.01); *A61K 8/06* (2013.01); *A61K 8/068* (2013.01); *A61K 8/894* (2013.01); *A61Q 19/00* (2013.01); *B01F 17/0014* (2013.01); *B01F 17/0028* (2013.01); *A61K 2800/21* (2013.01)

(58) Field of Classification Search
None
See application file for complete search history.

(56) References Cited

U.S. PATENT DOCUMENTS

| | | | | |
|---|---|---|---|---|
| 6,071,857 A | * | 6/2000 | Vogt et al. | 504/366 |
| 2001/0039321 A1 | * | 11/2001 | Kennedy et al. | 528/10 |
| 2007/0190012 A1 | * | 8/2007 | Feng et al. | 424/70.12 |
| 2008/0004357 A1 | * | 1/2008 | Meyer et al. | 516/54 |

FOREIGN PATENT DOCUMENTS

| | | |
|---|---|---|
| EP | 1136515 A2 | 9/2001 |
| JP | 03-181329 | 8/1991 |
| JP | 05-039202 | 2/1993 |
| JP | 2008-013554 | 1/2008 |

OTHER PUBLICATIONS

Wang L., Li X., Zhang G., Dong J. and Eastoe J., Oil-in-water nanoemulsions for pesticide formulations, J. Colloid and Interface Science 314: 230-235 (2007).*
Chaplin, 2009 "Kosmotropes and Chaotropes".*
Japanese Office Action in Japanese Patent Application No. 2009-187595, Mailing No. 629674, mailed Sep. 25, 2013.
Lijuan Wang et al., "Oil-in-water nanoemulsions for pesticide formulations", Journal of Colloid and Interface Science, 2007, 314, 230-235.
Wang et al: "Oil-in-water nanoemulsions for pesticide formulations", Journal of Colloid and Interface Science, Academic Press, New York, NY, US,; Bd. 314, Nr. 1, Aug. 6, 2007, Seiten 230-235,; XP022185576,; ISSN: 0021-9797, DOI: 10_1 016/J.JCIS.2007.04.079.
Solans C et al: "Nano-emulsions",; Current Opinion in Colloid and Interface Science, London, GB,; Bd. 10, Nr. 3-4, Oct. 1, 2005, Seiten 102-110,; XP027721299,; ISSN: 1359-0294.
Sadurni N et al: "Studies on the formation of O/W nano-emulsions, by low-energy emulsification methods, suitable for pharmaceutical applications",; European Journal of Pharmaceutical Sciences, Elsevier, Amsterdam, NL, Bd. 26, Nr.5, Dec. 1, 2005, Seiten 438-445, XP027803713, ISSN: 0928-0987.
European Search Report issued in EP 09 16 5855 mailed Jul. 15, 2014.

* cited by examiner

*Primary Examiner* — Sue Liu
*Assistant Examiner* — Thor Nielsen
(74) *Attorney, Agent, or Firm* — Frommer Lawrence & Haug

(57) ABSTRACT

Nanoemulsions and processes for their preparation, and their use as formulations of plant protection products and/or pesticides and/or cosmetic preparations.

21 Claims, 1 Drawing Sheet

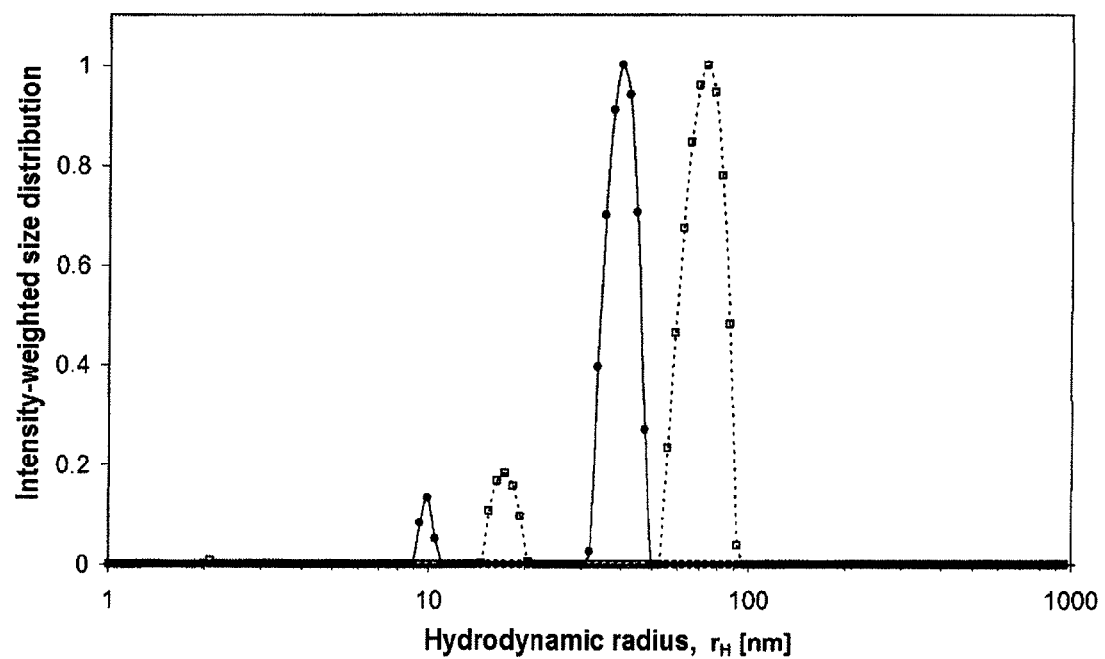
Results of the dynamic light scattering measurements of Example 4a (filled circles) and Example 4b (open squares)

NANOEMULSIONS AND PROCESSES FOR THEIR PREPARATION, AND THEIR USE AS FORMULATIONS OF PLANT PROTECTION AGENTS AND/OR PESTICIDES AND/OR COSMETIC PREPARATIONS

This application claims benefit under 35 U.S.C. 119(e) of U.S. Provisional Application Ser. No. 61/089,079, filed on 15 Aug. 2008.

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

An inexpensive and, in particular energy-efficient, process for the preparation of finely divided oil-in-water emulsions which have outstanding stability in wide temperature and concentration ranges is what is known as the PSQ (phase shift by quenching) process.

The PSQ process, which has been described in EP-A2-1 882 516 (U.S. Patent Appl. Pub. 2008-004357), is the process of choice for use in formulations of plant protection agents.

A first step of this process involves the lowering of what is known as the phase inversion temperature (PIT) of a microemulsion system down to at least room temperature or use temperature level by using cosmotropic substances, while, in a second step, the PIT is increased again, preferably to the original level, by adding diluents. During this procedure, the emulsion is retained, while undergoing a transition from a thermodynamically stable microemulsion to a kinetically stable nanoemulsion.

However, the PSQ process is not advantageous in all cases since it is frequently the case that plant-physiologically active salts must be employed as cosmotropic substances.

In the PSQ process, the cosmotropic substances replace the temperature increase step of the PIT process (Phase Inversion temperature, K. Shinoda; H. Kunieda, Encyclopedia of Emulsion Technology; Vol 1 (1983), p. 337ff). In the PIT process, the mixture of the components must be heated to above the phase inversion temperature in order to invert the O/W emulsion, which is present at room temperature, into a W/O emulsion and to prepare a finely divided O/W emulsion by subsequent rapid cooling. The energy consumption required for the heating and the efficient cooling steps is the considerable disadvantage of the PIT process, thereby making it largely uneconomical.

Adding sufficient amounts of diluents, according to the inversion preferably water or aqueous, optionally alcoholic, solutions, means that the concentration of the cosmotropic substances (CS) drops below the minimum concentration of the cosmotropic substances required for lowering the phase inversion temperature, so that the original temperature level is restored. Here, the diluting is carried out rapidly enough that no phase separation of the resulting nanoemulsion takes place, similar to what happens when the temperature drops rapidly.

Cosmotropic substances are understood as meaning those substances which favor, or enhance, the formation of hydrogen bonds in an aqueous phase. Thus, it is possible to shift the hydrophilicity/hydrophobicity of an amphiphilic substance towards a greater hydrophobicity by adding a cosmotropic substance.

By using cosmotropic substances, the temperature of one of the microemulsion phase boundaries, or indeed both temperatures of the microemulsion phase boundaries, are lowered to a lower level.

Examples of cosmotropic substances are mentioned in EP-A2-1 882 516; these water-soluble substances share the fact that they are ionic, salt-like in nature or else that they belong to the group of the likewise water-soluble organic acids or alcohols.

The PSQ and the PIT processes share the feature that the nanoemulsion obtained after diluting the microemulsion should be sufficiently "far" removed from the phase boundary to the microemulsion sector and thus remains "frozen". When a temperature near the phase boundary is reached, the nanoemulsion disintegrates with formation of large drops, and, ultimately, phase separation occurs.

Other processes for nanoemulsion formation, such as microfluidization and ultrasonication also generally disfavored as the processes are expensive and/or require high energy input. See Lawrence et al., "Recent Advances in Microemulsions as Drug Delivery Vehicles", Nanoparticulates as Drug Carriers, ed. V. P. Torchilin, publ. Imperial College Press, (2006).

Therefore, there remained the need for an inexpensive process for the preparation of finely divided emulsions which have outstanding stability in a wide temperature and concentration range, while largely overcoming the disadvantages of the PIT and the PSQ processes.

Accordingly, it was an aim of the basic invention to modify processes for the preparation of nanoemulsions, which processes are based on the dilution or the rapid cooling of microemulsions, so that the application of great temperature changes or the use of cosmotropic compounds can largely be dispensed with and that they, in a further embodiment, can be applied to the formulation of physiologically active compositions such as, for example, plant protection products and/or pesticides and/or cosmetic preparations and/or fungicidal preparations.

Surprisingly, it has now been found that nanoemulsions can be prepared by diluting microemulsions, where hydrophobic substances which are sparingly soluble or indeed insoluble in water, and therefore per se noncosmotropic substances, are used which are capable of obtaining a (cosmotrope-)analogous effect with regard to the temperature and which are capable of lowering at least one temperature of the microemulsion phase boundaries to a lower level.

The term "pseudo-cosmotropic" and its use is understood as meaning, for the purposes of the present application, a substance which is hydrophobic, which is therefore not present in the aqueous phase and which can thus not be considered to be a cosmotrope, but which, however, shifts the phase boundaries of a microemulsion like a cosmotrope, that is to say which acts like a cosmotrope with regard to the temperature.

The pseudo-cosmotropic, hydrophobic substances according to the invention are not only capable of lowering the phase boundary of a microemulsion, but additionally they result, surprisingly, also in the fact that the nanoemulsions obtained after dilution of the microemulsion are stable.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Accordingly, the invention relates to a process for the preparation of a nanoemulsion, where at least one hydrophobic pseudo-cosmotropic substance, at least one hydrophilic substance, at least one emulsifier, optionally one or the mixture of a plurality of hydrophobic oils, and, if appropriate, further adjuvants or auxiliaries are mixed with one another to give a microemulsion and thereafter diluted to give the nanoemulsion.

It is thereby possible to fully dispense with the addition of additional anions/cations or other organic compounds which are considered cosmotropes, or at least to reduce the concentration.

If appropriate, however, it is (still) possible concomitantly to use cosmotropic substances, for example in order to optimize the temperature profile in the microemulsions from technical points of view or, if appropriate, to add to the value of the emulsion by acting as micronutrients.

In contrast to cosmotropic substances which are present in the aqueous phase, the pseudo-cosmotropic substances according to the invention are not soluble in water and are present in the oily phase. For the purposes of the present invention, insoluble in water, or sparingly soluble in water, means a solubility in water of less than 1.0 g/l at 25° C., preferably less than 0.5 g/l and very especially preferably less than 0.1 g/l.

Interestingly, these pseudo-cosmotropic substances which have unexpectedly been found also include for example a multiplicity of plant protectants and/or pesticidal actives, specifically fungicides and insecticides.

Surprisingly, it has been found that, for example, pesticides or pesticide mixtures which themselves are sparingly soluble in water or not at all also bring about a shift in the phase boundary of the microemulsion just like a cosmotrope present in the water phase, and, in this manner, make possible the application of a process which is analogous to the PSQ process, i.e. which are advantageously suitable for the formulation of microemulsions from which subsequently nanoemulsions can be prepared by dilution.

What is especially surprising is the fact that the multiplicity of hydrophobic substances precisely also includes the physiologically active substances or compositions which, being pseudo-cosmotropic substances, are capable of lowering at least one of the temperatures of the microemulsion phase boundary to a lower level.

Substances which are employed are pesticidal actives or active mixtures, for example herbicides, fungicides, growth regulators, molluscicides, micronutrients and insecticides, all of which are sparingly soluble in water or not at all, preferably those which have a solubility in water of less than 1.0 g/l, in particular less than 0.5 g/l at 25° C. and especially preferably less than 0.1 g/l.

The chemical classes and constituents, or the composition, of active substances in connection with their use and fields of application are described for example in the 'The Pesticide Manual', 14th edition, 2006, The British Crop Protection Council, or in the 'The Manual of Biocontrol Agents', 2001, The British Crop Protection Council.

These substances or mixtures may contain further components which are usually concomitantly used in the preparation of pesticide compositions.

Pesticides from the following classes of substances may be mentioned by way of example, but not by way of limitation: pyrethroids, sulfonylureas, triazoles, morpholines, phenylpyrazoles, neonicotinoids, tetracyclins, cyclodienes, organochlorines, organophosphorus-based pesticides, carbamates and dithiocarbamates, phthalimides, strobilurins, benzimidazoles, aryloxyphenoxypropionates and/or triazines.

The process according to the invention extends in particular to abamectin (solubility in water 7-10 μg/l), tebuconazole (solubility in water 36 mg/l), nicosulfuron (solubility in water 0.07 g/l), niclosamide (solubility in water 0.1 g/l), tridemorph (solubility in water 1.1 mg/l), epoxyconazole (solubility in water $6.63*10^{-4}$ g/100 ml), bifenthrin (solubility in water <1 μg/l), permethrin (solubility in water $6\times10^{-3}$ mg/l), fipronil (solubility in water 1.9 mg/l), chlorpyrifos (solubility in water 1 mg/l), endosulfan (solubility in water 0.32 mg/l), mancozeb (solubility in water 6.2 ppm), captan (solubility in water 3.3 mg/l), azoxystrobin (solubility in water 6 mg/l), carbendazim (solubility in water 29 mg/l), clodinafop-propargyl (solubility in water 4 mg/l), atrazine (solubility in water 33 mg/l).

In order to avoid solvents which are unpleasant for the user with regard to labeling and odor, the main aim was to prepare microemulsions for the preparation of the nanoemulsions which can be used for spray mixtures, which microemulsions can be prepared readily and can be diluted with water as desired.

In plant protection, it is customary to employ what are known as adjuvants or else auxiliaries in order to improve the efficiency. These adjuvants or auxiliaries are either added to the aqueous spray mixture shortly before spraying (as a tank mix additive) or else incorporated directly into formulations. Tank mix additives reduce the surface tension of spray drops. This reduced surface tension over water (72 mN/m) brings about better penetration of the formulation across the hydrophobic leaf body, i.e. pesticides act better and are absorbed better, specifically by plants. Trisiloxanes and polysiloxanes are known for being capable of reducing the surface tension to <30 mN/m.

In order to save the additional pass of the tank mix additive, a further subject matter of the invention was to incorporate these adjuvants—also known as spreaders—into the microemulsions.

Substances which have proved advantageous for the adjuvants used in the microemulsions are those known as oil spreaders. These oil spreaders belong to the class of the organically modified polysiloxanes of the general formula (1):

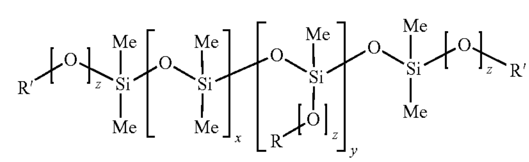

(1)

where z=independently of one another 0 or 1, x=0 to 200, preferably 5 to 150 and especially preferably 10 to 100,
y=0 to 100, preferably 1 to 35,
R'=R or an alkyl radical,
R=$(CH_2)_n$—$(O)_o$—$(C_2H_4O)_q(C_3H_6O)_q(C_2H_3LO)_{r-K}$ and/or $C_mH_{2m+1}$
m=1 to 40, preferably 1 to 30 and particularly preferably 8 to 24,
n=0, 3, 4 or 6, preferably 0 or 3
o=0 or 1,
p=0 to 50, preferably 0 to 25,
q=0 to 50, preferably 0 to 25,
r=0 to 50, preferably 0,
L=ethyl or phenyl,
K is H, an alkyl radical having 4 or fewer carbon atoms, or is an acetyl group,
with the proviso that the molecule must comprise at least one group R.

Further adjuvants which can also be used concomitantly within the scope of the compositions according to the invention are cosmotropic substances, for example for optimizing the temperature profile of the mixtures with a view to their use.

A key distinction between microemulsions and nanoemulsions is the type of stability. Whereas microemulsions are thermodynamically stable, nanoemulsions (also known as mini- or submicron emulsions) are kinetically stable. One means of confirming the different forms is by heating both the microemulsion and the nanoemulsion to about 90° C. or higher and followed by cooling. Whereas a nanoemulsion will show separation into distinct phases, the microemulsion, because it is thermodynamically stable is in a one phase again after just shaking the mixture.

The stability of the microemulsions should be ensured in a temperature range of between −10° C. and +90° C., preferably between 0° C. and 70° C. and especially preferably between +5° C. and 60° C.

Stability means, in the present context, that no crystallization and no phase separation occurs, that is, that a 1-phase system is always present.

The period of time over which the stability of the nanoemulsion must be ensured amounts to at least 24 hours, preferably at least 48 hours under use conditions, in each case at a temperature of at least 25° C.

The microemulsion should be storage-stable for at least 2 years, preferably at least 3 years and very preferably 5 years at 25° C.

The temperature range with regard to storage and transport is preferred, but also prescribed by the test method CIPAC MT 46, which describes the testing of the stability of plant protection formulations. The nanoemulsions which can be prepared by dilution with water have particle sizes of between 10 and 300, preferably between 20 and 250 nm and especially preferably between 30-200 nm.

A further subject matter of the present invention is a process for the preparation of a nanoemulsion by diluting a microemulsion which contains at least one hydrophobic, pseudo-cosmotropic substance within the meaning of the invention, comprising A) the preparation of a mixture 2 with at least one pseudo-cosmotropic substance, water, if appropriate an organo-modified polysiloxane, if appropriate a hydrophobic substance and at least one emulsifier, where at least one of the phase boundaries of the microemulsion phase of this mixture is at a lower temperature than the corresponding phase boundary of the microemulsion phase of a mixture 1 without a pseudo-cosmotropic substance, but otherwise with the same composition as mixture 2, and subsequently a step B) addition of a diluent to the mixture 2 in order to convert this mixture into a nanoemulsion 3, where the amount of the diluent added is chosen such that the nanoemulsion 3 obtained is not present in the form of a microemulsion phase at a preset temperature.

A further subject matter of the present invention are nanoemulsions where the microemulsions on which they are based contain the pseudo-cosmotropic substance in an amount of from 0.5 to 40% by weight, preferably from 2 to 30% by weight, especially preferably from 3 to 25% by weight.

A further subject matter of the present invention are nanoemulsions where the microemulsions on which they are based contain, besides the pseudo-cosmotropic substance, an oil or a plurality of oils which have a flash point of at least 110° C. and which are from the group of the mineral oils, aromatic oils, vegetable oils, fatty acid esters, liquid paraffins or silicone oils, as further hydrophobic substance.

In this context it is preferred to use hydrophobic oils, aliphatics from the group of the mineral oils and liquid paraffins or mixtures of these as the oil used.

A further subject matter of the present invention are nanoemulsions where the microemulsions on which they are based contain an additive which is based on an organo-modified polysiloxane of the general formula (1).

A further subject matter of the present invention are nanoemulsions where the microemulsions or which they are based are stable in a temperature range of within −10° C. and +90° C., specifically from 0° C. to 70° C., very especially of within +5° C. and 60° C.

A further subject matter of the present invention are nanoemulsions which are formed upon diluting a microemulsion whose average particle size distribution is in the range of from 10-300 nm, specifically 20-250 nm, very especially preferably between 30-200 nm, with water.

A further subject matter of the present invention are nanoemulsions which can be prepared by diluting microemulsions as desired with water in the ratio of from 1:3 to 1:10 000, preferably from 1:15 to 1:1000, especially preferably from 1:20 to 1:500, based on parts by weight, and which, in the nanoemulsion formed, have particle sizes which bring about a translucency.

A further subject matter of the present invention is the use of the nanoemulsions according to the invention containing a pseudo-cosmotropic substance which belongs to the pesticides and which is used in the crop and in the non-crop sectors.

Crop is understood as meaning the treatment of (useful) plants in the extended agricultural sector, while non-crop means the use in the home-and-garden sector, and also the control of pests for example on/in timber materials or else for example against lice.

A further subject matter of the present invention are nanoemulsions where the microemulsions on which they are based contain as pseudo-cosmotropic substances for example pesticides from the group of the pyrethroids (concentration in the formulation 0.5-40% by weight), sulfonylureas (concentration limit in the formulation 0.5-25% by weight), triazoles (concentration in the formulation 0.5-25% by weight), neonicotinoids (concentration in the formulation 0.5-20% by weight).

A further subject matter of the present invention are nanoemulsions, where the pesticide or pesticide mixture present in the microemulsion on which they are based is an insecticide.

A further subject matter of the present invention is the use of a nanoemulsion which contains one or more pesticides by dilution of a microemulsion, prepared by one of the above-mentioned processes according to the invention, as concentrate for the concomitant use in veterinary and/or pharmaceutical and/or cosmetic preparations, for example for controlling lice.

EP-A2-1 882 516 describes the term microemulsion as a thermodynamically stable emulsion. If this microemulsion is diluted rapidly with water, the resulting solution is no longer thermodynamically stable, but only kinetically stable. The linear momentum, upon collision, of the small droplets which are already present in the microemulsion is insufficient to bring about coalescence, so that no phase separation occurs, but an emulsion is retained; owing to the small droplet size within the nanometer range, they are referred to as nanoemulsions.

The advantage in a plant protection formulation, specifically a microemulsion and the nanoemulsion prepared therefrom, of not having to employ an additional cosmotrope is firstly that some of the ionic compounds mentioned in EP-A2-1 882 516 are used in crop protection as micronutrients. Specifically in applications, in which these cosmotropes are not required for the plant, they generate unduly high values, for example as regards the phosphate content; this may result in incompatibility, indeed in phytotoxin reactions, in plants.

Moreover, most of the emulsifier quantity in comparison with known processes and formulations can be dispensed with, and, despite this, a very rapid emulsification can be achieved, since the phase inversion temperature is lowered. Emulsification in the systems according to the invention takes place rapidly and even without employing mixers, where emulsification takes place under the effect of high shear forces.

In many applications, the use of cosmotropic substances is disadvantageous since a multiplicity of pesticides are ionic in effect, which means that the addition of such cosmotropes may lead to incompatibility reactions, for example precipitates may form in the formulation.

Another advantage of the formulations according to the invention is the fact that, when no additional cosmotropes are required, there is more room within the formulation for other components, and fairly concentrated formulations can be prepared. Also, the active ingredient, also referred to as the active, may be present in the formulation in considerably higher concentrations. This is advantageous not only with regard to the transport volume, but also the fact that unnecessary chemicals need not be applied, which is a good thing from the environmental point of view.

Microemulsions which can be employed for agrochemicals are described in PCT/US2004/007388 (U.S. Patent Appl. Publ. 2004-235668). The lipophilic emulsifiers described therein, which are frequently employed in the cosmetics sector, are expensive and should therefore not be used in the present basic microemulsion. It has also emerged that the use of lipophilic coemulsifiers is not necessary in the process described in the present invention.

As regards the emulsifiers on which the present invention is based, one uses increasingly ethoxylated fatty alcohols alone or in the form of mixtures. Typical emulsifiers are TEGO Alkanol L 4 ($C_{12}/C_{14}$ alcohol, ethoxylated), Rewopal LA 6 (lauryl alcohol polyethoxylate, n=6), Rewopal LA 10 (lauryl alcohol polyethoxylate, n=10), Rewopal LA 12-80 (aqueous solution of lauryl alcohol polyethoxylate, n=12), TEGO Alkanol L 23 P (lauryl alcohol polyethoxylate, n=23). A feature of the above is a pronounced temperature dependency—required for employing the PSQ process—since the hydrophilicity/hydrophobicity of the emulsifier depends on the extent of the hydrogen bridges formed in the aqueous phase. The number of the hydrogen bridges decreases with increasing temperature, so that the emulsifier becomes less hydrophilic, and the character of the emulsion is shifted from O/W towards W/O.

In comparison to alkyl polyglycosides (APGs) as they are used in PCT/US2004/007388, the above have a considerably lower tendency to foam, which is important when applying the aqueous spray mixture. APGs, in turn, are usually additionally combined with antifoams when making the spray mixture.

If required, the addition of antifoams to the microemulsion preparation described in the present invention is possible.

The process for the preparation of a composition according to the invention is carried out by simply stirring a mixture which contains at least one hydrophilic substance, for example water, at least one hydrophobic, pseudo-cosmotropic substance, for example a (plant-, animal-, insect- or else fungus-) physiologically active substance, if appropriate one or more hydrophobic oils and/or if appropriate an organomodified polysiloxane and at least one emulsifier.

Here, at least one temperature of the microemulsion phase boundaries of this mixture is at a lower temperature than the corresponding phase boundary of the microemulsion phase of a mixture which does not contain any physiologically active pseudo-cosmotropic substance. The formulation according to the invention thus obtained takes the form of a microemulsion. By adding a diluent, for example water, to such a microemulsion, the latter is converted into a nanoemulsion.

In principle, all those compounds as are used in the prior art as emulsifiers for the preparation of O/W and W/O emulsions are suitable as emulsifiers. It is preferred here to employ at least one emulsifier from the group of the ionic and of the nonionic emulsifiers.

In addition, the following representatives may be mentioned among the suitable emulsifier components from the known classes of substances, without laying claim to completeness:

Suitable nonionic emulsifiers here are in particular oligoalkoxylates whose basic molecules contain lipophilic residues. They can be derived in particular from selected representatives from the following classes of the basic molecules which contain lipophilic residues: fatty alcohols, fatty acids, fatty amines, fatty amides, esters and/or ethers of fatty acids and/or fatty alcohols, alkanolamides, alkylphenol and/or their reaction products with formaldehyde, and further reaction products of lipophilic-residue-containing basic molecules and lower alkoxides. As specified, the respective reaction products may also be end-capped, at least in part. Examples of partial esters and/or partial ethers of fully functional alcohols are, in particular, the corresponding partial esters with fatty acids, for example of the glycerol mono- and/or diester type, for example castor oil oleate, glycol monoesters, corresponding partial esters of oligomerized polyfunctional alcohols, sorbitan partial esters and the like, and corresponding compounds with ether groups. Such partial esters and/or partial ethers may in particular also be the basic molecules for an (oligo)alkoxylation.

It is preferred to employ ethylene oxide, propylene oxide, butylene oxide or styrene oxide in the alkoxylation process.

Especially preferred nonionic alkoxylated emulsifiers are:

adducts of 2 to 30 mol of ethylene oxide and/or 0 to 5 mol of propylene oxide on linear fatty alcohols having 8 to 22 C atoms, on fatty acids having 12 to 22 C atoms and on alkylphenols having 8 to 15 C atoms in the alkyl group;

glycerol monoesters and diesters and sorbitan monoesters and diesters of saturated and unsaturated fatty acids having 6 to 22 carbon atoms, and their ethylene oxide adducts;

alkyl monoglycosides and alkyl oligoglycosides having 8 to 22 carbon atoms in the alkyl radical, and their ethoxylated analogs.

The adducts of ethylene oxide and/or of propylene oxide on fatty alcohols, fatty acids, alkylphenols, glycerol monoesters and diesters and sorbitan monoesters and diesters of fatty acids, or on castor oil, are known, commercially available products. They take the form of homolog mixtures whose mean degree of alkoxylation corresponds to the weight ratio of ethylene oxide and/or propylene oxide to the substrate involved in the addition reaction; comb-like or end-modified silicone polyethers, as may be obtained for example by hydrosilylation reactions under known conditions by carrying out an addition reaction between alkene-functionalized polyethers and preferably 2 to 100 mol of ethylene oxide and/or propylene oxide. The terminal hydroxyl groups of such polyethers may optionally also be alkyl-terminated here (in particular methyl-terminated).

The following may furthermore be employed as nonionic emulsifiers:

polyol esters, in particular polyglycerol esters such as, for example, polyglycerol polyricinoleate or polyglycerol poly-12-hydroxystearate. Others which are suitable are mixtures of compounds from a plurality of these classes of substances; partial esters based on linear, branched, unsaturated or saturated $C_6/C_{22}$-fatty acids, ricinoleic acid and 12-hydroxystearic acid and glycerol, for example glycerol monodioleate, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

polysiloxane-polyalkyl-polyether copolymers or corresponding derivatives;

$C_8/C_{18}$-alkylmono- and -oligoglycosides, their preparation and their use as surface-active substances are disclosed for example in U.S. Pat. No. 3,839,318, U.S. Pat. No. 3,707,535, U.S. Pat. No. 3,547,828, DE-OS 19 43 689, DE-OS 20 36 472 (U.S. Pat. No. 3,772,269) and DE-A1 30 01 064 (U.S. Pat. No. 4,349,669) and also EP-A 0 077 167 (U.S. Pat. No. 4,923,976). They are prepared in particular by reacting glucose or oligosaccharides with primary alcohols having 8 to 18 C atoms.

Suitable emulsifiers with ionic character are anionic, cationic and zwitterionic emulsifiers. Anionic emulsifiers contain water-solubilizing anionic groups such as, for example, a carboxylate, a sulfate, a sulfonate or a phosphate group, and a lipophilic residue. Anionic surfactants are known to the skilled worker in large numbers and are commercially available. In particular, they take the form of alkyl sulfates or alkyl phosphates in the form of their alkali metal, ammonium or alkanolammonium salts, alkyl ether sulfates, alkyl ether carboxylates, acyl sarcosinates and sulfosuccinates and acyl glutamates in the form of their alkali metal or ammonium salts. It is also possible to employ di- and trialkyl phosphates, and mono-, di- and/or tri-PEG-alkyl phosphates and their salts.

Cationic emulsifiers may also be employed. Cationic emulsifiers which may be used are, in particular, quaternary ammonium compounds, such as alkyltrimethylammonium halides such as, for example, cetyltrimethylammonium chloride or bromide or behenyltrimethylammonium chloride, but also dialkyldimethylammonium halides such as, for example, distearyldimethylammonium chloride. It is furthermore possible to employ monoalkylamidoquats such as, for example, palmitamidopropyltrimethylammonium chloride, or corresponding dialkylamidoquats. It is furthermore possible to employ readily biodegradable quaternary esters compounds, which usually take the form of quaternized fatty acid esters which are based on mono-, di- or triethanolamine. Alkylguanidinium salts may furthermore be employed as cationic emulsifiers.

It is furthermore possible to use zwitterionic surfactants as emulsifiers. The term zwitterionic surfactants refers to those surface-active compounds which have at least one quaternary ammonium group and at least one carboxylate and one sulfonate group in the molecule. Zwitterionic surfactants which are particularly suitable are what are known as betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines with in each case 8 to 18 C atoms in the alkyl or acyl group, and cocoacylaminoethylhydroxyethylcarboxymethyl glycinate. Especially preferred is the fatty acid amide derivative known by the CTFA name cocamidopropylbetaine. Emulsifiers which are also suitable are ampholytic surfactants. Ampholytic surfactants are understood as meaning those surface-active compounds which, besides a $C_8/C_{18}$-alkyl or $C_8/C_{18}$-acyl group contain at least one free amino group and at least one —COOH— or —SO$_3$H group in the molecule and which are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids with in each case approximately 8 to 18 C atoms in the alkyl group. Especially preferred ampholytic surfactants are N-cocoalkyl aminopropionate, cocoacyl aminoethylaminopropionate and $C_{12}$-$C_{18}$-acylsarcosine. Besides the ampholytic emulsifiers, quaternary emulsifiers are also suitable, with those of the esterquat type, preferably methyl-quaternized difatty acid triethanolamine ester salts, being especially preferred.

As regards the ionic emulsifiers, one should make clear that an emulsifier is defined as a substance which is located at the boundary surface between the hydrophilic and the hydrophobic phase, and can therefore not be a cosmotropic substance.

Cosmotropic substances are substances which are present in the aqueous phase and which have an effect on the formation of the hydrogen bonds.

It is especially preferred to employ at least one alkoxylated nonionic emulsifier. In an especially preferred embodiment of the invention, this nonionic basic emulsifier, or the combination of a plurality of nonionic emulsifiers, can be combined with ionic emulsifier components.

All emulsifiers share the characteristic of forming the boundary surface between the hydrophilic and the hydrophobic substance which are to be emulsified. Thus, they do not behave like typical cosmotropic substances, which are preferentially located in the aqueous phase and not in the boundary surface.

Hydrophobic oils or solvents which are preferably used are vegetable oils such as rapeseed oil, sunflower oil, colza oil, soybean oil, fatty acid esters such as rapeseed acid methyl esters of the Agnique® series, and also methyl oleate or methyl laurate, or else cane sugar esters, aromatic hydrocarbons such as $C_1$-$C_6$ alkylbenzenes (toluene, xylene), white spirit, $C_9$-$C_{12}$ aromatics such as the Aromatic® series (Exxon), Isopar L and M, $C_1$-$C_6$-alkylnaphthalenes, and mixtures of aromatics such as the Solvesso® series from Exxon, mineral oils of the Shellsol® series, ketones such as acetophenone, isophorone, cyclohexanone and methyl ethyl ketone, aromatic, cycloaliphatic or aliphatic ethers such as tetrahydrofuran or methyl tert-butyl ether, N-substituted $C_1$-$C_{12}$-alkylpyrrolidones such as N-methylpyrrolidone, cyclic aliphatic hydrocarbons and aliphatic liquid paraffins such as kerosene or else OLEO FC®. Silicone oils are another possibility. However, mixtures of oils/solvents are yet another possibility.

Where the nanoemulsions of the invention are used in combination with veterinary and/or pharmaceutical and/or cosmetic preparations, the active ingredients may also include those ingredients known in the art which include, but is not limited to those ingredients described in Plumb's Veterinary Drug Handbook—5$^{th}$ Edition (2005), The Merck Index—14$^{th}$ Edition (2006) and International Cosmetic Ingredient Dictionary and Handbook—12$^{th}$ Edition (2008).

The formulations according to the invention and the process for their preparation are described hereinbelow by way of example, without limiting the invention to these examples of embodiments. If the following text specifies ranges, general formulae or classes of compounds, these are intended to embrace only not the respective ranges or groups of compounds which are explicitly mentioned, but also all those sub-ranges and sub-groups of compounds which can be obtained by selecting individual values (ranges) or compounds.

Further embodiments of the process according to the invention can be seen from the claims.

EXPERIMENTAL PART

In the examples specified hereinbelow, the present invention is described by way of example without the invention, whose range of application results from the totality of the description and the claims, being construed as being limited to the embodiments mentioned in the examples. Unless explicitly stated otherwise, all percentages are by weight. Processes for the Preparation of the Nano- and Microemulsion Example 1a Permethrin as Pseudo-Cosmotropic Hydrophobic Active Ingredient Preparation of a Nanoemulsion by Diluting a Microemulsion, prepared by simply combining and stirring the components in the composition as detailed in Table 1 hereinbelow:

| | Microemulsion [% by weight] | Nanoemulsion after dilution of the microemulsion 1:20 [% by weight] |
|---|---|---|
| Liquid paraffin (fluid liquid paraffin with a boiling point of 260° C.) | 36.97 | 1.85 |
| Water | 9.25 | 95.46 |
| Lauryl alcohol polyethoxylate (n = 6) | 29.57 | 1.47 |
| Lauryl alcohol polyethoxylate | 3.70 | 0.19 |

| | Microemulsion [% by weight] | Nanoemulsion after dilution of the microemulsion 1:20 [% by weight] |
|---|---|---|
| (n = 23) | | |
| Organo-modified polysiloxane (=cetyldimethicone) | 0.18 | 0.01 |
| Permethrin | 20.33 | 1.02 |
| Total | 100 | 100 |

Characterization:

The most frequent particle distribution or size distribution of the droplets (and all size distributions discussed hereinbelow) were determined with the aid of dynamic light scattering measurements (DLS). All light scattering measurements were carried out with dilute samples with an oil phase content of approx. 0.5% by weight (with oil phase referring to all components which are not water) at 25° C. using a Malvern HPPS 3.1, Malvern Instruments Ltd. The hydrodynamic radius $r_h$ is used to describe the particle size.

The most frequent particle size (radius) of the nanoemulsion of the example which forms the basis is approximately 82 nm. The dilution of the microemulsion with water 1:20 gives a nanoemulsion with a plant protectant content of approx. 1% by weight as is used in spray mixtures. A further dilution of 1:10 is carried out to bring the concentration of all nonaqueous components to a concentration of approx. 0.4% by weight (generally approx. 0.1-1.0% by weight), which is suitable for the light scattering.

To further characterize the microemulsion, the surface tension was measured neat, that is to say without dilution. The surface tension was determined by means of the pendent drop method (instrument: OCA 35 from Data Physics).

Here, he formulation of Example 1 has a surface tension of 23.5 mN/m. The same formulation, but without polysiloxane as adjuvant, shows a value of 30.0 mN/m.

The temperature range within which a homogeneous monophase microemulsion phase is present is determined by the following method: starting at room temperature (approx. 23° C.), the microemulsion mixture is warmed at a heating rate of approx. 3° C./min and stirred at moderate speeds with the aid of a magnetic stirrer. Any phase separation which takes place manifests itself first by the formation of microscopic droplets which lead to a refraction of the visible light and thus to a macroscopically visible cloudiness of the system. Upon cooling, the appearance of the mixture changes. When the temperature drops to or below the temperature below which the microemulsion mixture is present in a homogeneous, monophase microemulsion phase, it changes from cloudy to transparent.

The temperature of the lower phase boundary of the one-phase microemulsion range was determined by storage for one hour at various temperatures of between −5° C. and room temperature.

The temperature range of the microemulsion described in Example 1 is 5-80° C. (one-phase range). If the microemulsion is stored at −5° C., it solidifies, but regains its previous fluid transparent form after warming and storage at room temperature.

The storage stability of the nanoemulsion was determined by light scattering after storage for three days at different temperatures. At temperatures of up to 40° C., the droplet size increased slightly to approx. 100 nm. At 45° C., it increased to approx. 200 nm, which can be interpreted as the sign of incipient droplet coalescence.

Example 1b According to the Invention

If, in the formulation described in Example 1, no lauryl alcohol polyethoxylate (n=23) is used and if the ratio of the concentrations of the remaining components remains constant, then the microemulsion is monophase from below 5° C. to 69° C.

Comparative Example 1

Not According to the Invention

If, in the formulation described in Example 1a, no permethrin is used, then the microemulsion is monophase only from 69° C. (up to greater than 80° C.).

The permethrin in Example 1a therefore has a similar effect on the temperature as a cosmotrope and markedly lowers the temperature range of the monophase microemulsion.

Example 2

Permethrin as Pseudo-Cosmotropic Hydrophobic Active Ingredient

Preparation of a Nanoemulsion by Diluting a Microemulsion, prepared by simply combining and stirring the components in the composition as detailed in Table 2 hereinbelow:

|  | Microemulsion [% by weight] | Nanoemulsion after dilution of the microemulsion 1:100 [% by weight] |
|---|---|---|
| Liquid paraffin (fluid liquid paraffin with a boiling point of 260° C.) | 44.45 | 0.44 |
| Water | 11.11 | 99.12 |
| Lauryl alcohol polyethoxylate (n = 6) | 31.11 | 0.31 |
| Permethrin | 13.33 | 0.13 |
| Total | 100 | 100 |

Characterization:

The characterization regarding the emulsion drop size is carried out as described in Example 1. The most frequent particle size (radius) of the nanoemulsion of the example which forms the basis is approx. 42 nm. The dilution of the microemulsion with water 1:100 leads to a nanoemulsion with an active ingredient content of approx. 0.13% by weight. The concentration of all components which have an effect on light scattering was approx. 0.9% by weight (generally customarily approx. 0.1-1.0% by weight).

The temperature range within which a homogeneous monophase microemulsion phase is present is determined as specified in the process described in Example 1. The temperature range of the microemulsion described in Example 2 is 20-70° C. (monophase range).

If, in the formulation described in Example 2, lauryl alcohol polyethoxylate (n=6) is additionally used to lauryl alcohol polyethoxylate (n=23) in the ratio 1:8 (n=23 to n=6), and the ratio of the concentrations of the remaining components remains constant, then the microemulsion is monophase from 15° C. to above 80° C.

Upon comparing Examples 1 and 2, whose most pronounced difference is the permethrin concentration (almost twice the concentration in Example 1), while the total emulsifier concentration is constant, it emerges that permethrin markedly lowers the temperature of the upper phase boundary of the monophase range and therefore brings about a cosmotrope-analogous effect with regard to the temperature.

Example 3

Tebuconazole as Pseudo-Cosmotropic Hydrophobic Active Ingredient

Preparation of a Nanoemulsion by Diluting a Microemulsion, prepared by simply combining and stirring the components in the composition as detailed in Table 3 hereinbelow:

|  | Microemulsion [% by weight] | Nanoemulsion after dilution of the microemulsion 1:30 [% by weight] |
|---|---|---|
| Fatty acid tetraethylenepentamine | 37.74 | 1.26 |
| Water | 9.43 | 96.98 |
| Lauryl alcohol polyethoxylate (n = 6) | 37.74 | 1.26 |
| Tebuconazole | 15.09 | 0.50 |
| Total | 100 | 100 |

Characterization:

The characterization regarding the emulsion drop size is carried out as described in Example 1. The most frequent particle size (radius) of the nanoemulsion of the example which forms the basis is approx. 170 nm. The dilution of the microemulsion with water 1:30 leads to a nanoemulsion with an active ingredient content of approx. 0.5% by weight, corresponding to the use concentration for spray liquors. A further dilution of 1:6 is carried out in order to bring the concentration of all nonaqueous components to a concentration of approx. 0.5% by weight which is suitable for the light scattering (generally approx. 0.1-1.0% by weight).

The temperature range within which a homogeneous monophase microemulsion phase is present is determined as specified in the process described in Example 1. The temperature range of the microemulsion described in Example 3 is 5-80° C. (monophase range).

Example 4

Comparison of the Nanoemulsions Obtained by the Process According to the Invention and Obtained by the Pit Process 4a) Process According to the Invention The characterization regarding the emulsion drop size is carried out as described in Example 1. The most frequent particle size (radius) of the nanoemulsion of the example which forms the basis is approx. 40 nm (see FIG. 1, filled circles). The dilution of the microemulsion with water 1:100 leads to a nanoemulsion with an active ingredient content of approx. 0.05% by weight. The concentration of all nonaqueous components is approximately 0.8% by weight and is thus a concentration conventionally used for light scattering (generally approx. 0.1-1.0% by weight).

The temperature range within which a homogeneous monophase microemulsion phase is determined as specified in the process described in Example 1. The temperature range of the microemulsion described in Example 4a is 7-62° C. (monophase range).

4b) PIT Process

Preparation of a Nanoemulsion by the Pit Process by Simply combining and stirring the components and warming the mixture to 80° C. up to the monophase microemulsion range, followed by rapid cooling to room temperature (approx. 23° C.).

The characterization regarding the emulsion drop size is carried out as described in Example 1. The most frequent particle size (radius) of the nanoemulsion of the example which forms the basis is approx. 74 nm (see FIG. 1, open squares). The further dilution of the microemulsion by rapid cooling with water 1:100 leads to a nanoemulsion with an active ingredient content of approx. 0.05% by weight. The concentration of all nonaqueous components is approximately 0.8% by weight and is thus a concentration conventionally used for light scattering (generally approx. 0.1-1.0% by weight).

Conclusion from the Comparison of Examples 4a and 4b:

The process according to the invention allows the energy-efficient preparation of a storage-stable microemulsion whose particle size distribution is smaller than that of the microemulsions prepared by the PIT method. The nanoemulsions obtained therefrom by dilution are suitable as formulations of plant protectants and/or pesticides and/or cosmetic preparations.

BRIEF DESCRIPTION OF THE DRAWINGS

FIG. 1 shows the results of the dynamic light scattering measurements.

Having thus described in detail various embodiments of the present invention, it is to be understood that the invention defined by the above paragraphs is not to be limited to particular details set forth in the above description as many apparent variations thereof are possible without departing from the spirit or scope of the present invention.

We claim:

1. A process for preparing a nanoemulsion comprising:
   providing or obtaining a microemulsion comprising:
   at least one pseudo-cosmotropic substance which is sparingly soluble in water or insoluble in water, and which lowers a temperature of at least one phase boundary of the microemulsion to a lower level as compared to the microemulsion without the at least one pseudo-cosmotropic substance; and
   at least one oil spreader as an adjuvant, wherein the oil spreader is an organo-modified polysiloxane of the general formula (1):

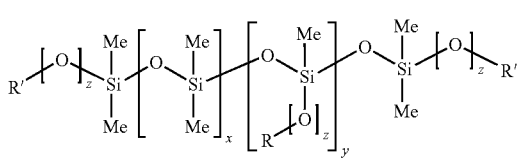

(1)

where:
z=independently of one another 0 or 1;
x=0 to 200;
y=0 to 100;
R'=R or an alkyl radical;

$R=(CH_2)_n-(O)_o-(C_2H_4O)_p(C_3H_6O)_q(C_2H_3LO)_r-K$ and/or $C_mH_{2m+1}$;
n=0, 3, 4 or 6;
o=0 or 1;
m=1 to 40;
p=0 to 50;
q=0 to 50;
r=0 to 50;
L=ethyl or phenyl; and
K is H, an alkyl radical having 4 or fewer carbon atoms, or is an acetyl group;
with the proviso that formula (1) must comprise at least one group R; and
diluting the microemulsion with water in a ratio of 1:20 to 1:10,000, based on parts by weight, to obtain the nanoemulsion;
wherein the nanoemulsion is storage stable and has an average particle size distribution in the range of from 10-200 nm for at least 48 hours at 40° C.; and
wherein the at least one pseudo-cosmotropic substance includes at least one substance selected from the group consisting of pesticidal actives.

2. The process as claimed in claim 1;
wherein the microemulsion further comprises:
at least one hydrophilic substance;
at least one emulsifier;
optionally one or more hydrophobic oils; and
optionally one or more further adjuvants or auxiliaries.

3. The process as claimed in claim 1;
wherein the pseudo-cosmotropic substance comprises a physiologically active substance or composition.

4. The process as claimed in claim 1;
wherein the microemulsion further comprises:
water;
at least one emulsifier; and
optionally a hydrophobic substance.

5. A nanoemulsion prepared by the process as claimed in claim 1;
wherein the pseudo-cosmotropic substance is employed in an amount of from 0.5 to 40% by weight of the total formulation of the microemulsion.

6. A nanoemulsion prepared by the process as claimed in claim 4;
wherein the microemulsion includes the hydrophobic substance; and
wherein the hydrophobic substance has a flash point of at least 110° C. and comprises at least one component selected from the group consisting of mineral oils, aromatic oils, vegetable oils, fatty acid esters, liquid paraffins and silicone oils, and mixtures thereof.

7. A nanoemulsion prepared by the process as claimed in claim 1.

8. A nanoemulsion prepared by the process as claimed in claim 4;
where the microemulsion is stable within a temperature range of between −10° C. and +90° C.

9. The nanoemulsion prepared by a process as claimed in claim 4;
wherein the average particle size distribution of the nanoemulsion is in the range of from 20-200 nm.

10. A nanoemulsion prepared by the process as claimed in claim 4;
wherein particle sizes of the nanoemulsion are present which bring about a translucency.

11. A nanoemulsion prepared by the process as claimed in claim 1;

wherein the pseudo-cosmotropic substance is a pesticide or pesticide mixture.

12. The nanoemulsion as claimed in claim 11;
wherein the pseudo-cosmotropic substance is an insecticide or insecticide mixture.

13. The nanoemulsion as claimed in claim 5;
wherein the pseudo-cosmotropic substance includes at least one pesticide or insecticide selected from the group consisting of pyrethroids, sulfonylureas, triazoles, morpholines, phenylpyrazoles, neonicotinoids, tetracyclines, cyclodienes, organochlorines, organophosphorus-based pesticides, carbamates and dithiocarbamates, phthalimides, strobilurins, benzimidazoles, aryloxyphenoxypropionates, triazines, and mixtures thereof.

14. The nanoemulsion as claimed in claim 5, further comprising:
a cosmotropic substance.

15. A method of protecting a plant against pests, comprising:
administering a pesticially effective amount of the nanoemulsion of claim 5 to a plant.

16. A method of providing pesticidal effect in a veterinary, pharmaceutical, or cosmetic preparation, comprising:
adding a pesticidally effective amount of the nanoemulsion of claim 5, which further comprises of one or more pesticides, to a veterinary, pharmaceutical, or cosmetic preparation.

17. The process as claimed in claim 1;
wherein the microemulsion is diluted with water in a ratio of 1:20 to 1:500, based on parts by weight.

18. The process as claimed in claim 1;
wherein the concentration of water in the microemulsion prior to dilution is from 9.25% to 11.11% by weight.

19. The process as claimed in claim 1;
wherein the pseudo-cosmotropic substance is permethrin.

20. The process as claimed in claim 1;
wherein the pseudo-cosmotropic substance is tebuconazole.

21. The process as claimed in claim 1;
wherein the pesticidal actives are selected from the group consisting of herbicides, fungicides, growth regulators, molluscicides, and insecticides.

* * * * *